United States Patent
Dhawan et al.

(10) Patent No.: US 8,188,316 B2
(45) Date of Patent: *May 29, 2012

(54) INTEGRATED PROCESS FOR THE PREPARATION OF POLYBENZIMIDAZOLE PRECURSORS

(75) Inventors: Rajiv Dhawan, Wilmington, DE (US); Joachim C. Ritter, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,757

(22) Filed: Dec. 10, 2009

(65) Prior Publication Data

US 2010/0160679 A1 Jun. 24, 2010

Related U.S. Application Data

(60) Provisional application No. 61/138,651, filed on Dec. 18, 2008.

(51) Int. Cl.
*C07C 211/00* (2006.01)
(52) U.S. Cl. ........ 564/441; 564/305; 564/306; 564/415; 564/416; 562/480
(58) Field of Classification Search .......................... None
See application file for complete search history.

(56) References Cited

U.S. PATENT DOCUMENTS

| 3,476,590 | A | | 11/1969 | Rabilloud |
| 3,783,137 | A | | 1/1974 | Gerber |
| 4,533,692 | A | * | 8/1985 | Wolfe et al. ................... 524/417 |
| 5,142,021 | A | | 8/1992 | Lysenko et al. |
| 6,040,478 | A | | 3/2000 | Sikkema et al. |

FOREIGN PATENT DOCUMENTS

| JP | 2003292476 | 10/2003 |
| JP | 2005330470 | 12/2005 |
| JP | 2005330471 | 12/2005 |

OTHER PUBLICATIONS

Dhawan et al., U.S. Appl. No. 12/634,745, filed Dec. 10, 2009.
Dhawan et al., U.S. Appl. No. 12/634,799, filed Feb. 22, 2010.
Dhawan et al., U.S. Appl. No. 12/634,825, filed Dec. 10, 2009.
Ritter et al. U.S. Appl. No. 12/634,730, filed Dec. 10, 2009, (Was U.S. Appl. No. 61/138,602).
Cotton and Wilkinson, Advanced Inorganic Chemistry, Periodic Table Only, 1966, Interscience Publishers, $2^{ND}$ Edition, New York.

* cited by examiner

*Primary Examiner* — Sudhakar Katakam
(74) *Attorney, Agent, or Firm* — Kevin S. Dobson (57) ABSTRACT

Processes are provided for preparing complexes of 2,3,5,6-tetraaminotoluene with an aromatic diacid where the aromatic diacid is insoluble in water under ambient conditions. An integrated process design starting with nitration of 2,6-dihalotoluene eliminates costly intermediate drying and recrystallization steps. Handling of solid materials with possible skin sensitizing properties and toxicity is avoided, thereby eliminating human and environmental exposure.

20 Claims, 2 Drawing Sheets

INTEGRATED PROCESS FOR THE PREPARATION OF POLYBENZIMIDAZOLE PRECURSORS

This application claims priority under 35 U.S.C. §119(e) from, and claims the benefit of, U.S. Provisional Application No. 61/138,651, filed Dec. 18, 2008, which is by this reference incorporated in its entirety as a part hereof for all purposes.

TECHNICAL FIELD

The disclosure relates to methods of making complexes of 2,3,5,6-tetraaminotoluene with aromatic diacids, which are then used to make high-performance polybenzimidazole polymers.

BACKGROUND

The synthesis of preferred polybenzimidazole based high performance fibers requires the selective condensation polymerization of 2,3,5,6-tetraaminotoluene ("TAT") with various substituted and unsubstituted aromatic diacids, such as 2,5-dihydroxyterephthalic acid ("DHTA"). A 1:1 complex formed between TAT and the aromatic diacid represents the monomer of choice for the production of a high molecular weight, high strength fiber, with this ratio being of utmost importance. These materials are typically prepared using aqueous conditions. However, when desired aromatic diacids with at most limited solubility in water are utilized, alternate conditions need to be developed. In addition, in identifying such alternate conditions, safety concerns, especially with respect to sensitizing properties of some intermediates, need to be addressed.

There thus remains a need for a safe, efficient process for the production of suitable high-purity TAT-diacid monomer complexes that can be polymerized to a high molecular weight polymer material for producing high-performance fibers.

SUMMARY

In one embodiment, this invention provides a process for preparing a complex of 2,3,5,6-tetraaminotoluene and an aromatic diacid, wherein the complex is generally described by Formula I

I wherein Ar is a divalent group containing one or two aromatic rings, wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:

a) providing a solution of 2,3,5,6-tetraaminotoluene (Formula II)

II in alcohol;

b) contacting the solution with a solution of an aromatic dicarboxylic acid generally described by Formula III

III in a solvent, wherein the solvent is selected from N,N-dimethylformamide, dimethylacetamide, N-methylpyrrolidone, and mixtures thereof; wherein the aromatic dicarboxylic acid is insoluble in water; and wherein the molar ratio of aromatic dicarboxylic acid to the 2,3,5,6-tetraaminotoluene salt is from 1:1 to 1.1:1; thereby producing and precipitating the complex generally described by Formula I; and c) cooling, filtering, and washing the precipitated complex.

In another embodiment, this invention provides an integrated process for preparing a complex of 2,3,5,6-tetraaminotoluene and an aromatic diacid, wherein the complex is generally described by Formula I

I wherein Ar is a divalent group containing one or two aromatic rings wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:

a) nitrating 2,6-dihalotoluene (II)

II wherein each Z is independently Cl or Br, in a reaction mixture comprising oleum or $SO_3$, nitric acid, and $H_2SO_4$ wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene;
(iii) the concentration of 2,6-dihalotoluene in the reaction mixture is between about 12 and about 24 weight percent; and wherein the temperature of the reaction mixture does not exceed 120° C.; thereby producing 2,6-dihalo-3,5-dinitrotoluene;

b) directly separating the 2,6-dihalo-3,5-dinitrotoluene from the reaction mixture by filtration, while recycling the sulfuric acid mother liquor;

c) washing the 2,6-dihalo-3,5-dinitrotoluene with water or acid then water, then with $NH_4OH$, and then mixing it with glycol as a suspension;

d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;

e) directly separating the 2,6-diamino-3,5-dinitrotoluene from the reaction mixture by filtration, washing with glycol, then washing with water, f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;

h) contacting the 2,3,5,6-tetraaminotoluene produced in (g) with an aqueous solution comprising 1 to 6 equivalents of acid per mol of 2,3,5,6-tetraaminotoluene, and optionally a co-solvent; optionally heating the solution, thereby dissolving the 2,3,5,6-tetraaminotoluene;

i) filtering the reaction mixture, thereby removing the spent hydrogenation catalyst;

j) adding base to the filtered reaction mixture, thereby precipitating 2,3,5,6-tetraaminotoluene;

k) dissolving the 2,3,5,6-tetraaminotoluene in alcohol, thereby forming a solution;

l) contacting the solution with a solution of an aromatic dicarboxylic acid generally described by Formula III in a solvent, wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1; thereby producing and precipitating the complex generally described by Formula I; and m) cooling, filtering, and washing the precipitated complex.

In another embodiment, this invention provides an integrated process for preparing a complex of 2,3,5,6-tetraaminotoluene and an aromatic diacid, wherein the complex is generally described by Formula I wherein Ar is a divalent group containing one or two aromatic rings wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:

a) nitration of 2,6-dihalotoluene (II)

wherein each Z is independently Cl or Br, in a reaction mixture comprising oleum or $SO_3$, nitric acid, and $H_2SO_4$ wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene;
(iii) the concentration of 2,6-dihalotoluene in the reaction mixture is between about 12 and about 24 weight percent; and wherein the temperature of the reaction mixture does not exceed 120° C.; thereby producing 2,6-dihalo-3,5-dinitrotoluene;

b) directly separating the 2,6-dihalo-3,5-dinitrotoluene from the reaction mixture by filtration, while recycling the sulfuric acid mother liquor;

c) washing the 2,6-dihalo-3,5-dinitrotoluene with water or acid then water, then with $NH_4OH$, and then mixing it with glycol as a suspension;

d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;

e) directly separating the 2,6-diamino-3,5-dinitrotoluene from the reaction mixture by filtration, washing with glycol, then washing with water, f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;

h) contacting the 2,3,5,6-tetraaminotoluene produced in (g) with an aqueous solution comprising 1 to 6 equivalents of acid per mol of 2,3,5,6-tetraaminotoluene and optionally a co-solvent; optionally heating the solution, thereby dissolving the 2,3,5,6-tetraaminotoluene;

i) filtering the reaction mixture, thereby removing the spent hydrogenation catalyst;

j) combining the filtered reaction mixture with an acid, thereby precipitating 2,3,5,6-tetraaminotoluene salt;

k) cooling, filtering, and washing the precipitated 2,3,5,6-tetraaminotoluene salt;

l) dissolving the washed 2,3,5,6-tetraaminotoluene salt in water;

m) contacting the 2,3,5,6-tetraaminotoluene salt with base, thereby converting the 2,3,5,6-tetraaminotoluene salt into 2,3,5,6-tetraaminotoluene;

n) dissolving the 2,3,5,6-tetraaminotoluene in alcohol, thereby forming a solution;

o) contacting the solution with a solution of an aromatic dicarboxylic acid generally described by Formula III in a solvent, wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1, thereby producing and precipitating the complex generally described by Formula I; and p) cooling, filtering, and washing the precipitated complex.

In another embodiment, this invention provides a composition of Formula IV.

In another embodiment, this invention provides a composition of Formula V.

BRIEF DESCRIPTION OF THE DRAWINGS

The invention is illustrated by way of example and not limitation in the accompanying figures.

DETAILED DESCRIPTION

The following description is exemplary and explanatory only and is not restrictive of the invention, as defined in the appended claims.

A process is provided for preparing a complex generally described by Formula I wherein Ar is a divalent group containing one or two aromatic rings, wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:

a) providing a solution of 2,3,5,6-tetraaminotoluene (Formula II)

in alcohol;

b) contacting the solution with a solution of an aromatic dicarboxylic acid generally described by Formula III in a solvent, wherein the solvent is selected from N,N-dimethylformamide, dimethylacetamide, N-methylpyrrolidone, and mixtures thereof; wherein the aromatic dicarboxylic acid is insoluble in water; and wherein the molar ratio of aromatic dicarboxylic acid to the 2,3,5,6-tetraaminotoluene salt is from 1:1 to 1.1:1; thereby producing and precipitating the complex generally described by Formula I; and c) cooling, filtering, and washing the precipitated complex.

In another embodiment, an integrated process is provided for preparing a complex of 2,3,5,6-tetraaminotoluene and an aromatic diacid, wherein the complex is generally described by Formula I, comprising the sequential steps under exclusion of oxygen:
a) nitrating 2,6-dihalotoluene (II)

II wherein each Z is independently Cl or Br, in a reaction mixture comprising oleum or SO$_3$, nitric acid, and H$_2$SO$_4$
wherein
(i) the concentration of nitric acid is about 2.0 to about 2.3 moles per mole of 2,6-dihalotoluene;
(ii) the concentration of SO$_3$ is about 1 to about 3 moles per mole of 2,6-dihalotoluene;
(iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with NH$_4$OH, and then mixing it with glycol as a suspension;
d) aminating the 2,6-dihalo-3,5-dinitrotoluene by heating the suspension formed in step (c) to a temperature in the range of about 100° C. to about 160° C. and contacting it with NH$_{3(g)}$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;
h) contacting the 2,3,5,6-tetraaminotoluene produced in (g) with an aqueous solution comprising 1 to 6 equivalents of acid per mol of 2,3,5,6-tetraaminotoluene, and optionally a co-solvent; optionally heating the solution, thereby dissolving the 2,3,5,6-tetraaminotoluene;
i) filtering the reaction mixture, thereby removing the spent hydrogenation catalyst;
j) adding base to the filtered reaction mixture, thereby precipitating 2,3,5,6-tetraaminotoluene;
k) dissolving the 2,3,5,6-tetraaminotoluene in alcohol, thereby forming a solution;
l) contacting the solution with a solution of an aromatic dicarboxylic acid generally described by Formula III in a solvent, wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1; thereby producing and precipitating the complex generally described by Formula I; and
m) cooling, filtering, and washing the precipitated complex.

In another embodiment, an integrated process is provided for preparing a complex of 2,3,5,6-tetraaminotoluene and an aromatic diacid,
wherein the complex is generally described by Formula I, comprising the sequential steps under exclusion of oxygen:
a) nitration of 2,6-dihalotoluene (II)

II wherein each Z is independently Cl or Br, in a reaction mixture comprising oleum or SO$_3$, nitric acid, and H$_2$SO$_4$
wherein
(i) the concentration of nitric acid is about 2.0 to about 2.3 moles per mole of 2,6-dihalotoluene;
(ii) the concentration of SO$_3$ is about 1 to about 3 moles per mole of 2,6-dihalotoluene;
(iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with NH$_4$OH, and then mixing it with glycol as a suspension;
d) aminating the 2,6-dihalo-3,5-dinitrotoluene by heating the suspension formed in step (c) to a temperature in the range of about 100° C. to about 160° C. and contacting it with NH$_{3(g)}$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;
h) contacting the 2,3,5,6-tetraaminotoluene produced in (g) with an aqueous solution comprising 1 to 6 equivalents of acid per mol of 2,3,5,6-tetraaminotoluene and optionally a co-solvent; optionally heating the solution, thereby dissolving the 2,3,5,6-tetraaminotoluene;

i) filtering the reaction mixture, thereby removing the spent hydrogenation catalyst;

j) combining the filtered reaction mixture with an acid, thereby precipitating 2,3,5,6-tetraaminotoluene salt;

k) cooling, filtering, and washing the precipitated 2,3,5,6-tetraaminotoluene salt;

l) dissolving the washed 2,3,5,6-tetraaminotoluene salt in water;

m) contacting the 2,3,5,6-tetraaminotoluene salt with base, thereby converting the 2,3,5,6-tetraaminotoluene salt into 2,3,5,6-tetraaminotoluene;

n) dissolving the 2,3,5,6-tetraaminotoluene in alcohol, thereby forming a solution;

o) contacting the solution with a solution of an aromatic dicarboxylic acid generally described by Formula III in a solvent;

wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1; thereby producing and precipitating the complex generally described by Formula I; and p) cooling, filtering, and washing the precipitated complex.

In additional embodiments, new compositions of the Formulas (IV) and (V) are provided.

In the context of this disclosure, a number of terms shall be utilized.

As used herein, the terms "TAT," "TAT free base" "2,3,5,6-tetraaminotoluene," and "2,3,5,6-tetraaminotoluene free base" each equivalently denote 2,3,5,6-tetraaminotoluene itself, rather than a salt or complex of 2,3,5,6-tetraaminotoluene.

As used herein, the term "TAT salt" or, equivalently, "2,3,5,6-tetraaminotoluene salt," denotes a compound formed by reaction of 2,3,5,6-tetraaminotoluene salt with an acid such as HCl, acetic acid, $H_2SO_4$, or $H_3PO_4$. One example of a TAT salt is TAT.4HCl.

As used herein, the term "Ar diacid" denotes the aromatic dicarboxylic acid generally described by Formula III.

As used herein, the term "oleum" denotes fuming sulfuric acid, which is anhydrous and is formed by dissolving excess sulfur trioxide ($SO_3$) into sulfuric acid.

As used herein, the term "fuming nitric acid" denotes concentrated nitric acid containing dissolved nitrogen dioxide.

As used herein, the term "net yield" of a product denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

As used herein, the term "insoluble" means a solubility of less than about 5 weight percent in the specified solvent at ambient temperature. For example, terephthalic acid, whose solubility in water (pH 7) is 0.017 g/100 mL, is insoluble.

The processes described herein allow the preparation of complexes of TAT with aromatic diacids which are insoluble in water.

Aromatic dicarboxylic acids suitable for the processes described herein are generally described by Formula III:

wherein Ar is a divalent group containing one or two aromatic rings which may contain one or more substituents in addition to the —COOH groups shown. Examples of such substituents include without limitation: OH, SH, methyl, ethyl, F, Cl, and Br.

In one embodiment, the aromatic diacid is selected from the group consisting of terephthalic acid, isophthalic acid, 2,6-naphthalenedicarboxylic acid, 1,5-naphthalenedicarboxylic acid, 2,5-dihydroxyterephthalic acid, 2-hydroxyterephthalic acid, 1,5-dihydroxy-2,6-naphthalenedicarboxylic acid, 1-hydroxy-2,6-naphthalenedicarboxylic acid, 2-hydroxy-1,5-naphthalenedicarboxylic acid, 2,6-dihydroxy-1,5-naphthalenedicarboxylic acid, 4,4'-biphenyldicarboxylic acid, 2,2'-dihydroxy-4,4'-biphenyldicarboxylic acid, 2-hydroxy-4,4'-biphenyldicarboxylic acid, and mixtures thereof. When the aromatic diacid is terephthalic acid, the complex described by Formula IV is produced.

When the aromatic diacid is 2,6-naphthalene dicarboxylic acid, the complex described by Formula V is produced.

V

The integrated process described herein is designed in such a way that solids handling is avoided. Filtered materials are transferred, without prior drying, in the form of suspension slurries in the solvent that is used for the respective reaction step. This process design thereby avoids costly drying processes. It also avoids the handling of solid materials with possible skin sensitizing properties and toxicity, and eliminates human and environmental exposure to them.

Figure 1:
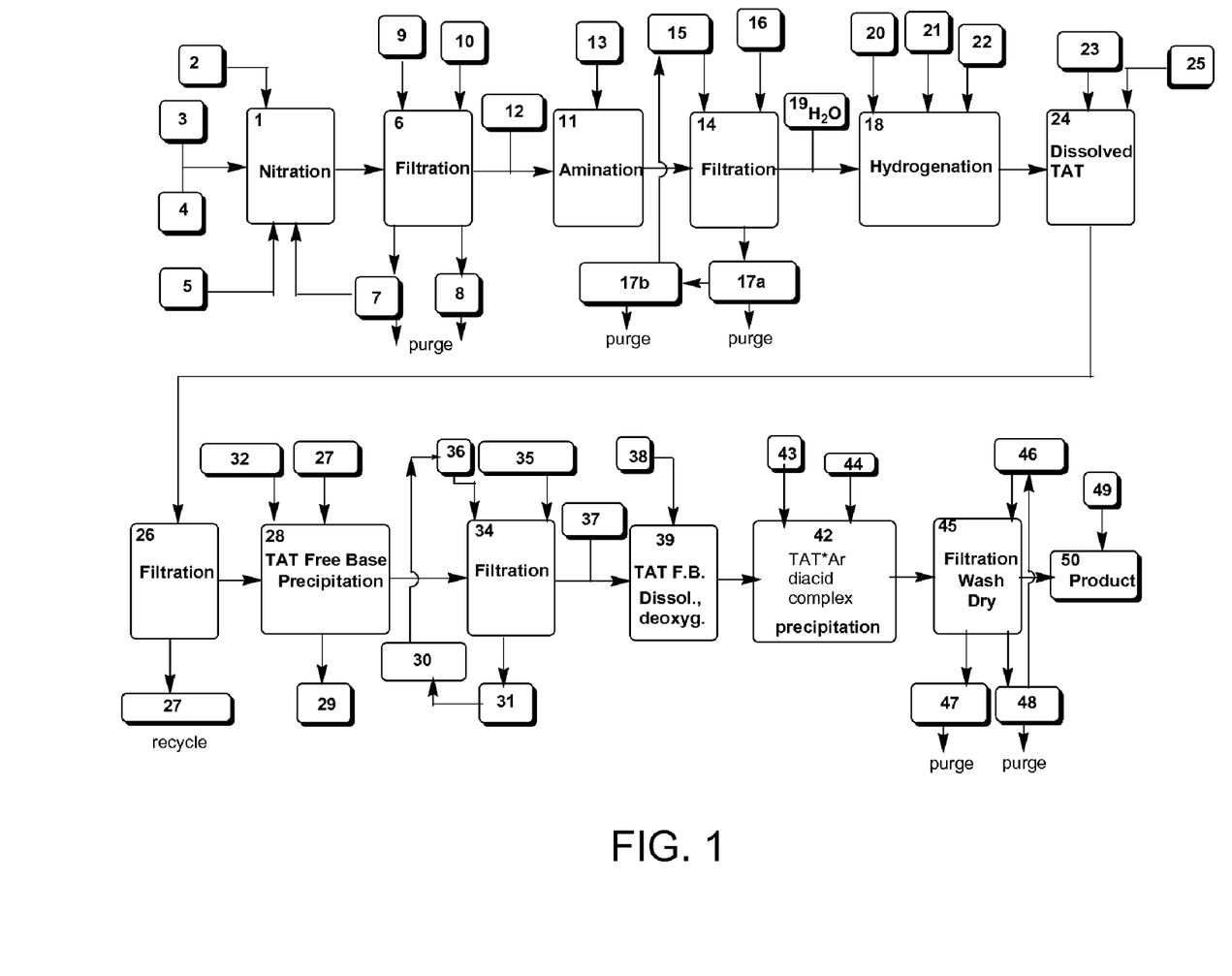
FIG. 1 is a schematic representation of one embodiment of the process described herein.

One embodiment of the integrated process described herein is illustrated in FIG. 1; possible minor modifications will be evident to one skilled in the art. With reference to the embodiment shown in FIG. 1, the process starts with the nitration 1 of 2,6-dihalotoluene, "mDHT" (i.e., 2,6-dichlorotoluene or 2,6-dibromotoluene; 2,6-dichlorotoluene is preferred), in a reaction mixture prepared by combining the 2,6-dihalotoluene 2; sulfuric acid; oleum 3 or $SO_3$ 5; and nitric acid 4. The concentration of nitric acid is about 2.0 to about 2.3 moles per mole of 2,6-dihalotoluene. Concentrated nitric acid (e.g., commonly used reagent grade, which is about 70% nitric acid in water) can be used, but fuming nitric acid is preferred. If concentrated nitric acid is used, since in the process described herein water must be kept at a level below one equivalent to get highly pure product, more $SO_3$ would be added to remove the water from the nitric acid (by reacting with it to form sulfuric acid) and still have sufficient $SO_3$ present in the reaction mixture for the nitration reaction. The concentration of $SO_3$ is about 1 to about 3 moles, preferably 1.5 to 2 moles, per mole of 2,6-dihalotoluene. The sulfuric acid is present in an amount such that the weight percent of mDHT in the reaction mixture (i.e., the weight of mDHT relative to the combined weight of mDHT plus the acid solution) is between 12 and 24 weight percent.

The nitration reaction is carried out at a temperature not to exceed about 120° C., typically in the range of about 5° C. to about 100° C., preferably in the range of about 5° C. to about 40° C., and more preferably in the range of about 5° to about 15° C. The 2,6-dihalo-3,5-dinitrotoluene thereby produced is separated directly by filtration 6 from the reaction mixture as a crude crystal cake without quench or recrystallization steps. The crude crystal cake is washed (9, 10) with water or with acid (e.g., concentrated or dilute sulfuric acid) then water; and is then washed with $NH_4OH$. Aqueous waste is discarded 8. The sulfuric acid mother liquor is recycled 7, 1 with a purge drawn to prevent excess sulfuric acid accumulation. The resulting wet cake of 2,6-dihalo-3,5-dinitrotoluene is then mixed with glycol 12 and introduced into the amination reactor 11 as a suspension.

The suspension is heated to a temperature in the range of about 100° C. to about 160° C., preferably about 140° C., to dissolve the 2,6-dihalo-3,5-dinitrotoluene in the glycol. The resulting solution is contacted at that temperature with gaseous $NH_3$ 13 for approximately four to eight hours close to ambient pressure; the $NH_3$ is fed as it is consumed. At reaction completion, the 2,6-diamino-3,5-dinitrotoluene thereby produced is filtered 14, typically at about 60° C., and washed with glycol 15 and then water 16. The mother liquor (filtrate) containing glycol is collected 17a, and the glycol is distilled and recycled 17b, 15; purges are drawn to prevent accumulation. The wet cake of 2,6-diamino-3,5-dinitrotoluene is slurried with water 19 and transferred to the hydrogenation reactor 18 as a suspension.

The hydrogenation reactor also contains a hydrogenation catalyst 22. Suitable hydrogenation catalysts comprise metal and/or metal salt; examples include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these, Pt/C is preferred. The catalyst is typically used in the amount of about 0.5 to about 5.0 wt % metal based on 2,6-diamino-3,5-dinitrotoluene.

The hydrogenation reactor is purged with nitrogen, and the aqueous suspension is contacted with hydrogen 21 in the presence of about 0 to about 1 mol equivalent of $NH_{3(g)}$ 20 to form a reaction mixture. The reaction is carried out at a temperature in the range of about to 20° C. to 100° C., preferably about 60° C. to about 85° C., and a hydrogen pressure of about 45 to about 500 psi (0.31 to 3.45 MPa) preferably about 300 psi (2.07 MPa). Reaction continues for a time sufficient to consume about 6 to 7 mol equivalents of hydrogen, thereby producing 2,3,5,6-tetraaminotoluene ("TAT"). The time required depends on the details of the specific set up but is typically about 2 hours.

As shown in FIG. 1, about 1 to about 6 equivalents, preferably about 1 to about 3 equivalents, of an acid 23 are added to dissolve the TAT; as a result, a solution of an acid salt of TAT is formed, herein referred to as "TAT salt." A small amount of tin (e.g., about 0.5 wt % tin powder) may be added as well to the solution to reduce oxidized species and prevent additional oxidation. Any acid which allows for the dissolution of TAT in water and its subsequent re-precipitation is suitable. The selection of the acid depends on the specific needs and is based on solubility data and is easily done by one skilled in the art. Examples of suitable acids include without limitation HCl, acetic acid, $H_2SO_4$, and $H_3PO_4$. HCl is preferred, and the TAT salt generally prepared is TAT.4HCl. The solution may be heated to facilitate dissolution. Optionally, a co-solvent may be present. Examples of co-solvents include without limitation methanol, ethanol, propanol, isopropanol, glycol, butanol, isobutanol, pentanol, hexanol, heptanol, octanol, and mixtures of these.

The resulting reaction mixture 24 is then filtered 25, typically at a temperature in the range of about 60° C. to about 80° C. to remove the spent hydrogenation catalyst 26, preferably by passing through a carbon filter bed. The spent catalyst can then be recycled.

Base, as a solid or in aqueous solution, is added 27 at a temperature in the range of about 0° C. to about 80° C. to form and precipitate the TAT free base 28. Examples of suitable bases include without limitation NaOH, KOH, LiOH, $Ca(OH)_2$, $NH_4OH$, sodium methoxide, and sodium ethoxide. NaOH is preferred. The amount of base needed for this step will depend on the concentration of TAT salt in the filtrate and is readily determined by one skilled in the art. Typically, about 4 to about 8 equivalents of base are needed in this step to precipitate the TAT free base in 64%-82% yield. Because of the sensitivity of TAT free base to oxygen, this precipitation is typically carried out under nitrogen 32. Aqueous wastes may be recovered 29, purified, and recycled.

The reaction mixture containing the precipitated TAT is then cooled to a temperature of about 5° C. to about 25° C. and stirred, then filtered 34. The TAT free base is then washed with deaerated water 35 and deaerated methanol 36. The used methanol can then be distilled 30 and recycled (31, 30, 36).

Hot alcohol (e.g., isopropanol at about 60° C. to about 82° C.), 37 is added to dissolve the TAT free base 39 under nitrogen 38. The TAT.Ar diacid complex (Formula I) is produced in vessel 42 by combining the deoxygenated TAT free base solution 39 with about 0.5 to about 1.5 equivalents of the Ar diacid solution 44. The Ar diacid 44, typically 0.5 to 1.0 equivalents, is dissolved in a solvent such as N,N-dimethylacetamide (DMAc), N-methylpyrrolidone (NMP), N,N-dimethylformamide (DMF) or mixtures of these; DMF is preferred. The temperature of the Ar diacid solution is about 75° C. to about 150° C., but typically about 95° C. In the embodiment shown in FIG. 12, the TAT free base solution 39 is added to the stirring solution of the diacid 44 in vessel 42. The temperature of the resulting mixture can be between 75° C. to about 150° C., but is typically about 90° C. to about 110° C. The mixture is then gradually cooled to promote complete precipitation of the complex. Various designs are possible for combining the TAT salt solution with the Ar diacid. FIG. 1 shows one embodiment in which a stream of TAT free base in alcohol solution 39 and the Ar diacid solution 44 are fed concurrently or consecutively into a vessel 42 wherein complex formation and precipitation take place. What design is best for a specific situation will be evident to one of skill in the art. The TAT salt solution and the Ar diacid are combined under a nitrogen atmosphere 43 to exclude oxygen. The preferred precipitation temperature will depend on the product concentration and on the amount of impurities present, but is generally chosen between about 0° and about 60° C., preferably between about 0° and about 25° C.

The TAT.Ar diacid complex is recovered from the reaction mixture by filtration 45 at a temperature in of the range of about 0° C. to about 60° C., preferably about 0° C. to about 25° C., and washed with methanol 46, typically at a temperature in the range of about 15° C. to about 40° C. The methanol is recycled 48 and a purge is drawn to prevent accumulation. The diacid solvent (e.g., DMF) and alcohol (e.g., isopropanol) wastes may also be recovered 47 and recycled. The washed and dried TAT.Ar diacid complex 50 is kept under nitrogen 49 to protect it from oxygen. It is of high enough quality and purity to produce polybenzimidazole polymer of high enough molecular weight to make high performance fibers.

In another embodiment (FIG. 2), the reaction mixture 24 is filtered 25, typically at a temperature in the range of about 60° C. to about 80° C. to remove the spent hydrogenation catalyst 26, preferably by passing through a carbon filter bed. The spent catalyst can then be recycled.

Figure 2:
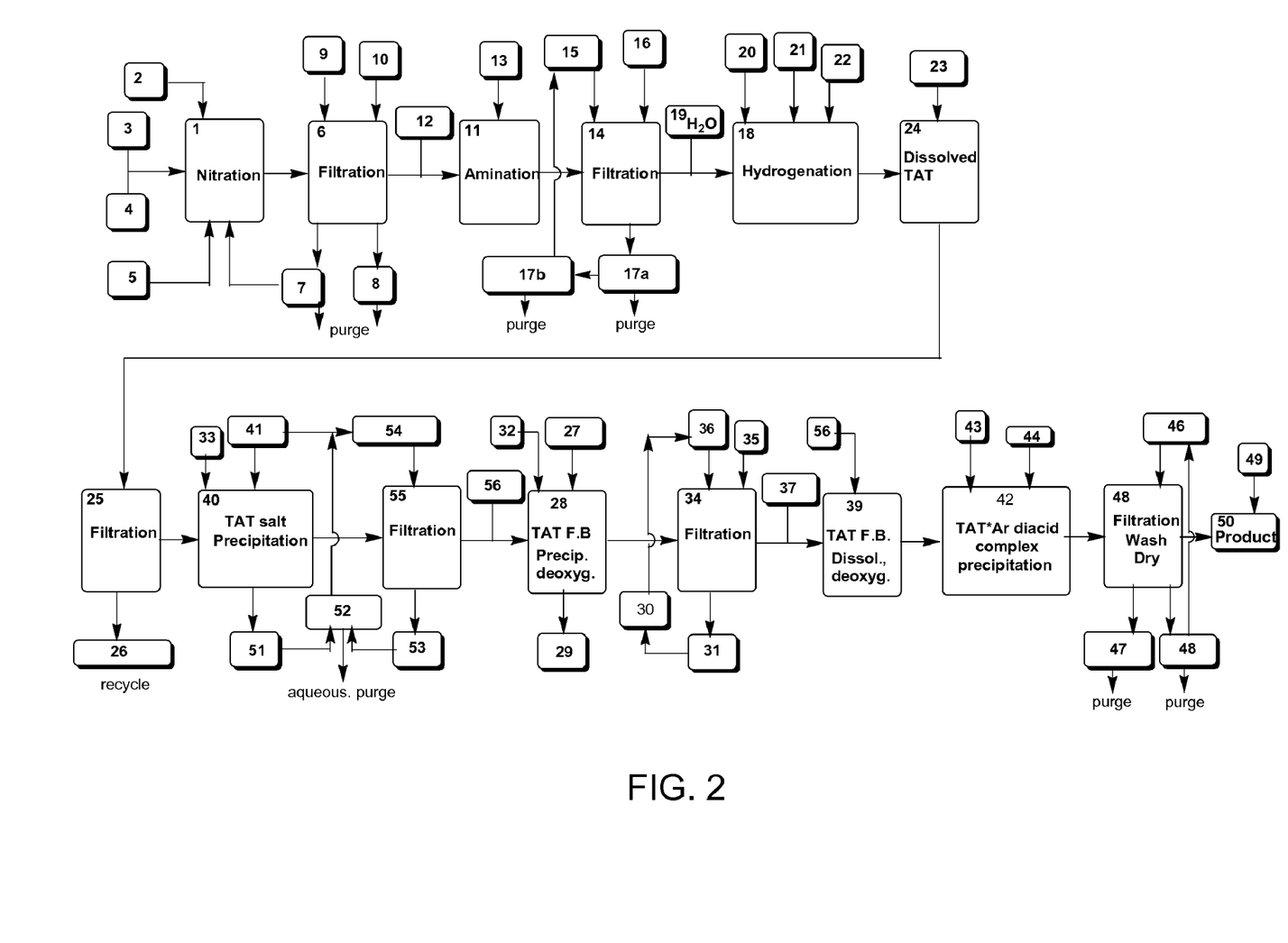
FIG. 2 is a schematic representation of a second embodiment of the process described herein.

A small amount of tin 33 (e.g., about 0.5 wt % tin powder) may be added as well to reduce oxidized species and prevent additional oxidation. Acid is added 41 at a temperature in the range of about 10° C. to about 80° C. to form and precipitate the TAT salt 40, for example, TAT.4HCl. Examples of suitable acids include without limitation HCl, acetic acid, $H_2SO_4$, and $H_3PO_4$. HCl is preferred. The amount of acid needed for this step will depend on the concentration of TAT in the filtrate and is readily determined by one skilled in the art. Typically, about 6 to about 8 equivalents of acid (for example, 38% $HCl_{aq}$) are needed in this step to precipitate the TAT salt (for example, TAT.4HCl) in about 90% yield. The use of gaseous acid, such as gaseous HCl, may reduce the total volume of liquid needed since the additional introduction of water with aqueous acid in both addition steps increases the absolute solubility of the TAT salt in the filtered reaction mixture. The addition of equivalent amounts of acid in the gas phase instead of as an aqueous solution (for example, $HCl_{gas}$ instead of $HCl_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 51, distilled 52, and recycled (52, 41) or used in the acid wash step of the process (52, 54).

The reaction mixture containing the precipitated TAT salt is then cooled to a temperature in the range of about 5° C. to about 15° C. and stirred, then filtered 55. The TAT salt is then washed with deaerated aqueous acid, such as concentrated HCl 54. The used aqueous acid can then be recovered 53, distilled 52, and recycled (52, 54).

Water at a temperature in the range of about 15° C. to about 35° C. is added 56 to dissolve the washed TAT salt 28. Although filtration 55 and salt dissolution 28 are shown as occurring in separate vessels in the embodiment illustrated in FIG. 2, a single vessel could be used. Because the filtered reaction mixture may have picked up small amounts of oxygen, nitrogen 32 is typically blown through it 28 in a deoxygenation step.

Base, as a solid or in aqueous solution, is added 27 at a temperature in the range of about 0° C. to about 80° C. to form and precipitate the TAT free base 28. Examples of suitable bases include without limitation NaOH, KOH, LiOH, $Ca(OH)_2$, $NH_4OH$, sodium methoxide, and sodium ethoxide. NaOH is preferred. The amount of base needed for this step will depend on the concentration of TAT in the filtrate and is readily determined by one skilled in the art. Typically, about 4 to about 8 equivalents of base are needed in this step to precipitate the TAT free base in 64%-82% yield. Aqueous wastes may be recovered 29, purified, and recycled.

The reaction mixture containing the precipitated TAT is then cooled to a temperature in the range of about 5° C. to about 25° C. and stirred, then filtered 34. The TAT free base is then washed with deaerated water 35 and deaerated methanol 36. The used methanol can then be recovered 31, distilled 30, and recycled (30,36).

Hot alcohol (e.g., isopropanol at about 60° C. to about 82° C.) 37 is added to dissolve the TAT free base 39 under nitrogen 38. The TAT.Ar diacid complex (Formula I) is produced by combining the deoxygenated TAT free base solution 39 with about 0.5 to about 1.5 equivalents of the Ar diacid solution 44. The diacid, typically 0.5 to 1.0 equivalents, is dissolved in a solvent such as N,N-dimethylacetamide (DMAc), N-methylpyrrolidone (NMP), N,N-dimethylformamide (DMF) or mixtures of these; DMF is preferred. The temperature of the Ar diacid solution is about 75° C. to about 150° C., but typically 95° C. In the embodiment shown in FIG. 2, the TAT free base solution 39 is added to the stirring solution of the diacid 44 in a vessel 42. The temperature of the mixture can be in the range of about 75° C. to about 150° C., but is typically about 90° C. to about 110° C. The mixture is then gradually cooled to promote complete precipitation of the complex. Various designs are possible for combining the TAT salt solution with the Ar diacid. FIG. 2 shows one embodiment in which a stream of TAT free base in alcohol solution 39 and the Ar diacid solution 44 are fed concurrently or consecutively into a vessel 42 wherein complex formation and precipitation take place. What design is best for a specific situation will be evident to one of skill in the art. The TAT salt solution and the Ar diacid are combined under a nitrogen atmosphere 43 to exclude oxygen. The preferred precipitation temperature will depend on the product concentration and on the amount of impurities present, but is generally chosen between about 0° and about 60° C., preferably between about 0° and about 25° C.

The TAT.Ar diacid complex is recovered from the reaction mixture by filtration 45 at a temperature in of the range of about 0° C. to about 60° C., preferably about 0° C. to about 25° C., and washed with methanol 46, typically at a temperature in the range of about 15° C. to about 40° C. The methanol is recovered, distilled 48, and recycled (48, 46), and a purge is drawn to prevent accumulation. The diacid solvent (e.g., DMF) and alcohol (e.g., isopropanol) wastes may also be recovered 52 and recycled. The washed and dried TAT.Ar diacid complex 50 is kept under nitrogen 49 to protect it from oxygen. It is of high enough quality and purity to produce polybenzimidazole polymer of high enough molecular weight to make high performance fibers.

The process described herein is an efficient and effective way to produce high purity TAT.Ar diacid complexes, particularly the 1:1 complexes of TAT and terephthalic acid and of TAT and 2,6-naphthalenedicarboxylic acid, which can be used to make polybenzimidazole polymer for high performance fibers. This process design eliminates costly intermediate drying and recrystallization steps. The recycling of spent catalyst and of sulfuric acid, glycol, and methanol streams contributes economical and environmental advantages. And, importantly, handling of solid materials with possible skin sensitizing properties and toxicity is avoided, thereby eliminating human and environmental exposure.

The materials, methods, and examples herein are illustrative only and, except as specifically stated, are not intended to be limiting.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

The meaning of abbreviations is as follows: ""g" means gram(s)," "DMF" means N,N-dimethylformamide, "2,6N" means 2,6-naphthalenedicarboxylic acid, "$^1$H-NMR" means proton nuclear magnetic resonance spectroscopy, "L" means liter(s), "mL" means milliliter(s), "min" means minutes, "mmol" means millimole(s), "T" means terephthalic acid, and "TAT" means 2,3,5,6-tetraaminotoluene.

Example 1

Preparation of 2,3,5,6-Tetraaminotoluene Tetrahydrochloride

This example demonstrates the preparation of TAT.4HCl from 2,6-diamino-3,5-dinitrotoluene.

A 1 L stirred Hastelloy autoclave was charged with 119 g of crude DADNT wet cake (about 0.49 mol), and 2.4 g of 5% Pt/C catalyst. The autoclave was purged 5 times with $N_2$ and 2 times with $H_2$ at 90 psi (0.62 MPa). Subsequently, 600 mL of deaerated water (purged with $N_2$ overnight) was added and the mixture was pressurized at 81° C. to 300 psi (2.07 MPa). Hydrogenation was continued for a total time of 3 h with an approximate uptake of 6.5 mol equivalents of $H_2$. The excess hydrogen was released and the autoclave was cooled to 40° C. and purged twice with $N_2$, after which 240 g of deaerated $HCl_{aq}$ (34%, by titration) was added. The mixture was stirred and heated back up to 80° C., then passed through a carbon bed filter at 75° C. to remove catalyst and a small amount of unconverted starting material. A total of about 1.0 L of a red-orange colored reaction solution was collected containing an equivalent of approximately 134 g of TAT.4HCl. (0.45 mol).

Example 2

Preparation of 2,3,5,6-Tetraaminotoluene Free Base 2,3,5,6-tetraaminotoluene tetrahydrochloride (TAT.4HCl) (60.59 g, 203.28 mmol) from Example 1 was added to a 1 L vessel and dissolved in deaerated water (300 g). Tin powder (0.360 g, 3.05 mmol) was added to this mixture and it was stirred for 10 minutes. NaOH (48.79 g, 1219.7 mmol) was added to 45 mL of deaerated water, allowed to cool to room temperature and then added to the stirring TAT.4HCl solution. The solution was stirred for 2 hours and free base TAT precipitated out of the solution as the solution cooled down to room temperature (18 hours). The precipitate was recovered by filtration, and washed with deaerated water (20 mL) and deaerated methanol (20 mL). This resulted in a crystalline beige solid being isolated in 82% yield (25.2 g). $^1$H-NMR analysis indicated TAT product purity was >99%.

Example 3

Preparation of TAT.2,6N from 2,3,5,6-Tetraaminotoluene and 2,6-Naphthalenedicarboxylic Acid 2,6-Naphthalenedicarboxylic acid (2,6N) (6.38 g, 29.52 mmol) was added to a 1 L bottle followed by the addition of N,N-dimethylformamide (DMF) (240 g) and the mixture stirred and heated to 95° C. internal temperature. Isopropanol (480 g) was heated to 82° C. and 2,3,5,6-tetraaminotoluene (TAT) (4.94 g, 32.47 mmol) (TAT) free base was dissolved in the heated isopropanol to form a solution, which was then added over a period of 5 minutes to the rapidly stirring solution of 2,6N in DMF at 95° C. to form a reaction mixture. The reaction mixture was stirred for 2 hours and then allowed to cool over 24 hours to room temperature, filtered, washed with methanol and dried in vacuo. This resulted in a yellow solid being isolated in 94% yield (10.21 g). $^1$H-NMR analysis indicated product purity was >99% with a TAT:2,6N ratio of 1.00:1.00.

Example 4

Preparation of TAT.T from 2,3,5,6-Tetraaminotoluene and Terephthalic Acid

Terephthalic acid (T) (7.04 g, 42.375 mmol) (T) was added to a 1 L bottle followed by the addition of N,N-dimethylformamide (DMF) (111 g) and the mixture stirred and heated to 95° C. internal temperature. Isopropanol (420 g) was heated to 82° C. and 2,3,5,6-tetraaminotoluene (TAT) free base was dissolved in the heated isopropanol to form a solution, which was then added over a period of 2 minutes to the rapidly stirring solution of T in DMF at 95° C. to form a reaction mixture. The reaction mixture was stirred for 2 hours and then allowed to cool over 24 hours to room temperature, filtered, washed with methanol (50 mL) and dried in vacuo. This resulted in a yellow crystalline solid being isolated in a net 91% yield (12.12 g). $^1$H-NMR analysis indicated product purity was >99% with a TAT:T ratio of 1.00:1.02.

Example 5

Preparation of 2,3,5,6-Tetraaminotoluene Free Base Wet Cake 2,3,5,6-Tetraaminotoluene tetrahydrochloride (TAT.4HCl) aqueous solution (100 g) obtained from Example 1 (equivalent to 29.8 g of 1,6-diamino-3,5-dinitrotoluene) was added to a 500 mL vessel along with tin powder (0.401 g, 3.375 mmol). This mixture was stirred for 10 minutes. NaOH (27 g, 675 mmol) was added to 45 mL of deaerated water, allowed to cool to room temperature and then added to the stirring TAT.4HCl solution to form a reaction mixture. The reaction mixture was stirred for 30 minutes and free base TAT precipitated out of solution as the reaction mixture was cooled down to 15° C. The precipitate was recovered by filtration, and washed with deaerated water (20 mL) and deaerated methanol (20 mL). This wet cake was used for Examples 6 and 7. A dried sample of the precipitate revealed the overall yield of the crystalline white solid to be 64% yield (10.92 g). $^1$H-NMR analysis indicated product purity was >99%.

Example 6

Preparation of TAT.T from 2,3,5,6-Tetraaminotoluene and Terephthalic Acid Wet Cake Terephthalic acid (T) (1.226 g, 7.38 mmol) was added to a 100 mL bottle followed by the addition of N,N-dimethylformamide (DMF) (21 g) and the mixture stirred and heated to 95° C. internal temperature. Isopropanol (60 g) was heated to 82° C. and 2,3,5,6-tetraaminotoluene (TAT) free base wet cake (equivalent to dried 1.20 g, 7.897 mmol) that was prepared in Example 5 was dissolved in the heated isopropanol to form a solution, which was then added over a period of 2 minutes to the rapidly stirring solution of T in DMF at 95° C. to form a reaction mixture. The reaction mixture was stirred for 2 hours and then allowed to cool over 24 hours to room temperature, filtered, washed with methanol (10 mL) and dried in vacuo. This resulted in a yellow crystalline solid being isolated in a net 72% yield (1.69 g). $^1$H-NMR analysis indicated product purity >99% with a TAT:T ratio of 1.00:1.00.

Example 7

Preparation of TAT.2,6N from 2,3,5,6-Tetraaminotoluene and 2,6-Naphthalenedicarboxylic Acid 2,6-Naphthalenedicarboxylic acid (2,6N) (1.595 g, 7.38 mmol) was added to a 100 mL bottle followed by the addition of N,N-dimethylformamide (DMF) (21 g) and the mixture stirred and heated to 95° C. internal temperature. Isopropanol (60 g) was heated to 82° C. and 2,3,5,6-tetraaminotoluene (TAT) free base wet cake (equivalent to dried 1.156 g, 7.601 mmol) that was prepared in Example 5 was dissolved in the heated isopropanol to form a solution, which was then added over a period of 5 minutes to the rapidly stirring solution of 2,6N in DMF at 95° C. The solution was stirred for 2 hours and then allowed to cool over 24 hours to room temperature, filtered, washed with methanol (10 mL) and dried in vacuo. This resulted in a yellow solid being isolated in 77% yield (2.09 g). $^1$H-NMR analysis indicated product purity was >99% with a TAT:2,6N ratio of 1.00:1.00.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

Certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

What is claimed is:

1. A process for preparing a complex of 2,3,5,6-tetraaminotoluene and an aromatic diacid, wherein the complex is generally described by Formula I wherein Ar is a divalent group containing one or two aromatic rings, wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:
  a) providing a solution of 2,3,5,6-tetraaminotoluene (Formula II)

in alcohol;
  b) contacting the solution with a solution of an aromatic dicarboxylic acid generally described by Formula III in a solvent,
    wherein the solvent is selected from N,N-dimethylformamide, dimethylacetamide, N-methylpyrrolidone, and mixtures thereof; wherein the aromatic dicarboxylic acid is insoluble in water; and wherein the molar ratio of aromatic dicarboxylic acid to the 2,3,5,6-tetraaminotoluene salt is from 1:1 to 1.1:1; thereby producing and precipitating the complex generally described by Formula I; and
  c) cooling, filtering, and washing the precipitated complex.

2. The process of claim 1 wherein the alcohol in step (a) is isopropanol and the temperature of the isopropanol is in the range of about 60° C. to about 82° C.

3. The process of claim 1 wherein the aromatic dicarboxylic acid is selected from the group consisting of terephthalic acid, isophthalic acid, 2,6-naphthalenedicarboxylic acid, 1,5-naphthalenedicarboxylic acid, 2,5-dihydroxyterephthalic acid, 2-hydroxyterephthalic acid, 1,5-dihydroxy-2,6-naphthalenedicarboxylic acid, 1-hydroxy-2,6-naphthalenedicarboxylic acid, 2-hydroxy-1,5-naphthalenedicarboxylic acid, 2,6-dihydroxy-1,5-naphthalenedicarboxylic acid, 4,4'-biphenyldicarboxylic acid, 2,2'-dihydroxy-4,4'-biphenyldicarboxylic acid, 2-hydroxy-4,4'-biphenyldicarboxylic acid, and mixtures thereof.

4. The process of claim 1 wherein the solvent in step (b) is N,N-dimethylformamide and the aromatic dicarboxylic acid is terephthalic acid, 2,6-naphthalenedicarboxylic acid, or a mixture thereof.

5. An integrated process for preparing a complex of 2,3,5,6-tetraaminotoluene and an aromatic diacid, wherein the complex is generally described by Formula I wherein Ar is a divalent group containing one or two aromatic rings wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:
  a) nitrating 2,6-dihalotoluene (II)

wherein each Z is independently Cl or Br, in a reaction mixture comprising oleum or $SO_3$, nitric acid, and $H_2SO_4$
    wherein
      (i) the concentration of nitric acid is about 2.0 to about 2.3 moles per mole of 2,6-dihalotoluene;
      (ii) the concentration of $SO_3$ is about 1 to about 3 moles per mole of 2,6-dihalotoluene;
      (iii) the concentration of 2,6-dihalotoluene in the reaction mixture is between about 12 and about 24 weight percent; and
    wherein the temperature of the reaction mixture does not exceed 120° C.; thereby producing 2,6-dihalo-3,5-dinitrotoluene;
  b) directly separating the 2,6-dihalo-3,5-dinitrotoluene from the reaction mixture by filtration, while recycling the sulfuric acid mother liquor;
  c) washing the 2,6-dihalo-3,5-dinitrotoluene with water or acid then water, then with $NH_4OH$, and then mixing it with glycol as a suspension;
  d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;
  e) directly separating the 2,6-diamino-3,5-dinitrotoluene from the reaction mixture by filtration, washing with glycol, then washing with water, f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;

h) contacting the 2,3,5,6-tetraaminotoluene produced in (g) with an aqueous solution comprising 1 to 6 equivalents of acid per mol of 2,3,5,6-tetraaminotoluene, and optionally a co-solvent; optionally heating the solution, thereby dissolving the 2,3,5,6-tetraaminotoluene;

i) filtering the reaction mixture, thereby removing the spent hydrogenation catalyst;

j) adding base to the filtered reaction mixture, thereby precipitating 2,3,5,6-tetraaminotoluene;

k) dissolving the 2,3,5,6-tetraaminotoluene in alcohol, thereby forming a solution;

l) contacting the solution with a solution of an aromatic dicarboxylic acid generally described by Formula III in a solvent, wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1; thereby producing and precipitating the complex generally described by Formula I; and m) cooling, filtering, and washing the precipitated complex.

6. The process of claim 5 wherein the alcohol in step (k) is isopropanol and the temperature of the isopropanol is in the range of about 60° C. to about 82° C.

7. The process of claim 5 wherein the aromatic dicarboxylic acid is selected from the group consisting of terephthalic acid, isophthalic acid, 2,6-naphthalenedicarboxylic acid, 1,5-naphthalenedicarboxylic acid, 2,5-dihydroxyterephthalic acid, 2-hydroxyterephthalic acid, 1,5-dihydroxy-2,6-naphthalenedicarboxylic acid, 1-hydroxy-2,6-naphthalenedicarboxylic acid, 2-hydroxy-1,5-naphthalenedicarboxylic acid, 2,6-dihydroxy-1,5-naphthalenedicarboxylic acid, 4,4'-biphenyldicarboxylic acid, 2,2'-dihydroxy-4,4'-biphenyldicarboxylic acid, 2-hydroxy-4,4'-biphenyldicarboxylic acid, and mixtures thereof.

8. The process of claim 5 wherein the solvent in step (l) is N,N-dimethylformamide and the aromatic dicarboxylic acid is terephthalic acid, 2,6-naphthalenedicarboxylic acid, or a mixture thereof.

9. The process of claim 5 further comprising adding Sn powder to the aqueous solution in step (h).

10. The process of claim 5 wherein the co-solvent in step (h) is selected from the group consisting of methanol, ethanol, propanol, isopropanol, glycol, butanol, isobutanol, pentanol, hexanol, heptanol, octanol, and mixtures of these.

11. An integrated process for preparing a complex of 2,3,5,6-tetraaminotoluene and an aromatic diacid, wherein the complex is generally described by Formula I wherein Ar is a divalent group containing one or two aromatic rings wherein said one or two aromatic rings may contain one or more substituents in addition to the —COOH groups shown, wherein said one or more substituents are selected from the group consisting of OH, SH, methyl, ethyl, F, Cl, and Br; comprising the sequential steps under exclusion of oxygen:

a) nitration of 2,6-dihalotoluene (II)

wherein each Z is independently Cl or Br, in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene;
(iii) the concentration of 2,6-dihalotoluene in the reaction mixture is between about 12 and about 24 weight percent; and wherein the temperature of the reaction mixture does not exceed 120° C.; thereby producing 2,6-dihalo-3,5-dinitrotoluene;

b) directly separating the 2,6-dihalo-3,5-dinitrotoluene from the reaction mixture by filtration, while recycling the sulfuric acid mother liquor;

c) washing the 2,6-dihalo-3,5-dinitrotoluene with water or acid then water, then with $NH_4OH$, and then mixing it with glycol as a suspension;

d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;

e) directly separating the 2,6-diamino-3,5-dinitrotoluene from the reaction mixture by filtration, washing with glycol, then washing with water;

f) forming a slurry of the 2,6-diamino-3,5-dinitrotoluene with water and transferring the slurry to a hydrogenation reactor containing a hydrogenation catalyst to form a reaction mixture;

g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;

h) contacting the 2,3,5,6-tetraaminotoluene produced in (g) with an aqueous solution comprising 1 to 6 equivalents of acid per mol of 2,3,5,6-tetraaminotoluene and optionally a co-solvent; optionally heating the solution, thereby dissolving the 2,3,5,6-tetraaminotoluene;
i) filtering the reaction mixture, thereby removing the spent hydrogenation catalyst;
j) combining the filtered reaction mixture with an acid, thereby precipitating 2,3,5,6-tetraaminotoluene salt;
k) cooling, filtering, and washing the precipitated 2,3,5,6-tetraaminotoluene salt;
l) dissolving the washed 2,3,5,6-tetraaminotoluene salt in water;
m) contacting the 2,3,5,6-tetraaminotoluene salt with base, thereby converting the 2,3,5,6-tetraaminotoluene salt into 2,3,5,6-tetraaminotoluene;
n) dissolving the 2,3,5,6-tetraaminotoluene in alcohol, thereby forming a solution;
o) contacting the solution with a solution of an aromatic dicarboxylic acid generally described by Formula III in a solvent,
wherein the aromatic dicarboxylic acid is insoluble in water; wherein the solvent is selected from N,N-dimethylformamide, N,N-dimethylacetamide, N-methylpyrrolidone, and mixtures thereof; and wherein the molar ratio of aromatic dicarboxylic acid to the 2,3,5,6-tetraaminotoluene salt is from 1:1 to 1.1:1, thereby producing and precipitating the complex generally described by Formula I; and
p) cooling, filtering, and washing the precipitated complex.

12. The process of claim 11 wherein the alcohol in step (n) is isopropanol and the temperature of the isopropanol is in the range of about 60° C. to about 82° C.

13. The process of claim 11 wherein the aromatic dicarboxylic acid is selected from the group consisting of terephthalic acid, isophthalic acid, 2,6-naphthalenedicarboxylic acid, 1,5-naphthalenedicarboxylic acid, 2,5-dihydroxyterephthalic acid, 2-hydroxyterephthalic acid, 1,5-dihydroxy-2,6-naphthalenedicarboxylic acid, 1-hydroxy-2,6-naphthalenedicarboxylic acid, 2-hydroxy-1,5-naphthalenedicarboxylic acid, 2,6-dihydroxy-1,5-naphthalenedicarboxylic acid, 4,4'-biphenyldicarboxylic acid, 2,2'-dihydroxy-4,4'-biphenyldicarboxylic acid, 2-hydroxy-4,4'-biphenyldicarboxylic acid, and mixtures thereof.

14. The process of claim 11 wherein the solvent in step (o) is N,N-dimethylformamide and the aromatic dicarboxylic acid is terephthalic acid, 2,6-naphthalenedicarboxylic acid, or a mixture thereof.

15. The process of claim 11 further comprising adding Sn powder to the aqueous solution in step (h) and/or in step (j).

16. The process of claim 11 wherein the co-solvent in step (h) is selected from the group consisting of methanol, ethanol, propanol, isopropanol, glycol, butanol, isobutanol, pentanol, hexanol, heptanol, octanol, and mixtures of these.

17. A composition comprising a monomeric complex of Formula IV or Formula V,

IV

V obtained by a process comprising the sequential steps under exclusion of oxygen:
a) providing a solution of 2,3,5,6-tetraaminotoluene (Formula II)

II in alcohol:
b) contacting the solution with a solution of an aromatic dicarboxylic acid generally described by Formula III

III in a solvent, wherein the solvent is selected from N,N-dimethylformamide, dimethylacetamide, N-methylpyrrolidone, and mixtures thereof; wherein the aromatic dicarboxylic acid is insoluble in water; and wherein the molar ratio of aromatic dicarboxylic acid to the 2,3,5,6-tetraaminotoluene salt is from 1:1 to 1.1:1; thereby producing and precipitating the complex generally described by Formula I; and
c) cooling, filtering, and washing the precipitated complex.

18. The composition of claim 17 wherein the tetraaminotoluene solution of step a) is obtained by a process comprising sequential steps under exclusion of oxygen:
(i) nitrating 2,6-dihalotoluene (I)

I wherein each Z is independently Cl or Br, in a reaction mixture comprising oleum or SO$_3$ nitric acid and H$_2$SO$_4$ wherein
(1) the concentration of nitric acid is about 2.0 to about 2.3 moles per mole of 2,6-dihalotoluene;
(2) the concentration of $SO_3$ is about 1 to about 3 moles mer mole of 2,6-dihalotoluene;
(3) the concentration of 2,6-dihalotoluene in the reaction mixture is between about 12 and about 24 weight percent; and wherein the temperature of the reaction mixture does not exceed 120° C.; thereby producing 2,6-dihalo-3,5-dinitrotoluene;

(ii) directly separating the 2,6-dihalo-3,5-dinitrotoluene from the reaction mixture by filtration, while recycling the sulfuric acid mother liquor;

(iii) washing the 2,6-dihalo-3,5-dinitrotoluene with water or acid then water, then with $NH_4OH$ and then mixing it with glycol as a suspension;

(iv) aminating the 2,6-dihalo-3,5-dinitrotoluene by heating the suspension formed in step (iii) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;

(v) directly separating the 2,6-diamino-3,5-dinitrotoluene from the reaction mixture by filtration, washing with glycol, then washing with water, (vi) forming a slurry of the 2,6-diamino-3,5-dinitrotoluene with water and transferring the slurry to a hydrogenation reactor containing a hydrogenation catalyst to form a reaction mixture;

(vii) hydrogenating the 2,6-diamino-3,5-dinitrotoluene by contacting the reaction mixture formed in step (vi) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraaminotoluene;

(viii) contacting the 2,3,5,6-tetraaminotoluene produced in (vii) with an aqueous solution comprising 1 to 6 equivalents of acid per mol of 2,3,5,6-tetraaminotoluene, and optionally a co-solvent; optionally heating the solution, thereby dissolving the 2,3,5,6-tetraaminotoluene;

(ix) filtering the reaction mixture, thereby removing the spent hydrogenation catalyst.

19. The process of claim 18 further comprising the steps of:
(x) adding base to the filtered reaction mixture, thereby precipitating 2,3,5,6-tetraaminotoluene; and,
(xi) dissolving the 2,3,5,6-tetraaminotoluene in alcohol, thereby forming the solution of step a).

20. The process of claim 18 further comprising the steps of:
(x) combining the filtered reaction mixture with an acid, thereby precipitating 2,3,5,6-tetraaminotoluene salt;
(xi) cooling, filtering, and washing the precipitated 2,3,5,6-tetraaminotoluene salt;
(xii) dissolving the washed 2,3,5,6-tetraaminotoluene salt in water;
(xiii) contacting the 2,3,5,6-tetraaminotoluene salt with base, thereby converting the 2,3,5,6-tetraaminotoluene salt into 2,3,5,6-tetraaminotoluene; and dissolving the 2,3,5,6-tetraaminotoluene in alcohol, thereby forming the solution of step a).

* * * * *